(12) United States Patent
Sagner et al.

(10) Patent No.: US 8,744,777 B2
(45) Date of Patent: *Jun. 3, 2014

(54) METHOD FOR REAL-TIME QUANTIFICATION OF NUCLEIC ACIDS

(75) Inventors: Gregor Sagner, Penzberg (DE); Karim Tabiti, Poecking (DE); Martin Gutekunst, Eberfing (DE); Richie Soong, Tutzing (DE)

(73) Assignee: Roche Molecular Systems, Inc., Pleasanton, CA (US)

( * ) Notice: Subject to any disclaimer, the term of this patent is extended or adjusted under 35 U.S.C. 154(b) by 49 days.

This patent is subject to a terminal disclaimer.

(21) Appl. No.: 13/163,500

(22) Filed: Jun. 17, 2011

(65) Prior Publication Data
US 2012/0270222 A1    Oct. 25, 2012

Related U.S. Application Data

(63) Continuation of application No. 12/549,150, filed on Aug. 27, 2009, now Pat. No. 8,024,132, which is a continuation of application No. 10/746,993, filed on Dec. 24, 2003, now abandoned, which is a continuation of application No. 09/823,711, filed on Mar. 30, 2001, now Pat. No. 6,691,041.

(30) Foreign Application Priority Data

Mar. 31, 2000    (EP) ..................................... 00107036
Jul. 13, 2000    (DE) .................................... 10034209

(51) Int. Cl.
*G01N 33/48*    (2006.01)
*G06F 19/00*    (2011.01)

(52) U.S. Cl.
CPC ..................................... *G06F 19/00* (2013.01)
USPC .......................................................... 702/19

(58) Field of Classification Search
None
See application file for complete search history.

(56) References Cited

U.S. PATENT DOCUMENTS

| | | | |
|---|---|---|---|
| 2,516,655 | A | 7/1950 | Smith |
| 3,163,404 | A | 12/1964 | Kraft et al. |
| 3,614,434 | A | 10/1971 | Horwitz |
| 3,711,379 | A | 1/1973 | Adams |
| 5,499,872 | A | 3/1996 | Baxter |
| 5,580,524 | A | 12/1996 | Forrest et al. |
| 5,858,658 | A | 1/1999 | Haemmerle et al. |
| 6,143,496 | A | 11/2000 | Brown et al. |
| 6,174,670 | B1 | 1/2001 | Wittwer et al. |
| 6,232,079 | B1 | 5/2001 | Wittwer et al. |
| 6,235,504 | B1 | 5/2001 | Zhang et al. |
| 6,691,041 | B2 | 2/2004 | Sagner et al. |
| 7,125,691 | B2 | 10/2006 | Sagner et al. |
| 7,378,241 | B2 | 5/2008 | Sagner et al. |
| 2002/0058262 | A1 | 5/2002 | Sagner et al. |

FOREIGN PATENT DOCUMENTS

| | | |
|---|---|---|
| EP | 0 640 828 A1 | 8/1994 |
| EP | 0 959 140 A1 | 6/1999 |
| EP | 1 138 784 A2 | 2/2001 |
| WO | WO 97/46707 A1 | 12/1997 |
| WO | WO 99/54510 A1 | 10/1999 |

OTHER PUBLICATIONS

Klein et al. (Electrophoresis, 1999, vol. 20, p. 291-299).*
Bishop et al. (Immunology and Cell Biology, 1997, vol. 75, p. 142-147).*
Freeman et al. (BioTechniques, 1999, vol. 26, p. 112-125).*
Bishop et al., "Quantitative reverse transcriptase-PCR amplification of a cytokine mRNA in a liver biopsy using a non-competitive method," (1997) *Immunology and Cell Biology* 75:142-147.
Bourinbaiar et al., "Simple Procedure for Estimating the Efficiency of PCR," *Molecular Biotechnology* (1996) 6:87-90.
Fink et al., "Real-time quantitative RT-PCR after laser-assisted cell picking," 1998, *Nature Medicine*, vol. 4, No. 11, pp. 1329-1333.
Freeman et al., "Quantitative RT-PCR: pitfalls and potential," 1999, *BioTechniques*, vol. 26, pp. 112-125.
Fujii et al., "Mutation Detection by TaqMan-Allele Specific Amplification: Application to Molecular Diagnosis of Glycogen Storage Disease Type Ia and Medium Chain Acyl-CoA Dehydrogenase Deficiency," *Human Mutation* (2000) 15:189-196.
Gibson et al., "A Novel Method for Real-Time Quantitative RT-PCR," (1996) *Genome Research* 6:995-1001.
Isono K. "A Novel Quantitative PCR With Fluorogenic Probe," *The Japanese Journal of Clinical Pathology*, (1997) 45 218-223 Abstract.
Klein et al., "Proviral load determination of different feline immunodeficiency virus isolates using real-time polymerase chain reaction: Influence of mismatches on quantification," (1999) *Electrophoresis* 20:291-299.
LightCycler System. Roche Molecular Biochemicals (1999) 1-6.
Meijerink et al. "A novel method to compensate for different amplification efficiencies between patient DNA samples in quantitative real-time PCR," (2001) *J Mol Diagnostics*, 3(2): 55-61.
Ririe et al., "Product Differentiation by Analysis of DNA Melting Curves during the Polymerase Chain Reaction," (1997) *Analytical Biochemistry* 245:154-160.
Rodriguez-Antona et al., "Quantitative RT-PCR Measurement of Human Cytochrome P-450s: Application to Drug Induction Studies," (2000) *Archives of Biochemistry and Biophysics* 376:109-116.
Zachar et al., "Absolute quantification of target DNA: a simple competitive PCR for efficient analysis of multiple samples," 1993, *Nucleic Acids Research*, vol. 21, pp. 2017-2018.

* cited by examiner

*Primary Examiner* — Pablo S Whaley
(74) *Attorney, Agent, or Firm* — Kilpatrick Townsend & Stockton LLP

(57) ABSTRACT

The present invention concerns a method for the quantification of a target nucleic acid in a sample comprising the following steps: (i) determination of the amplification efficiency of the target nucleic acid under defined amplification conditions, (ii) amplification of the target nucleic acid contained in the sample under the same defined reaction conditions, (iii) measuring the amplification in real-time, (iv) quantification of the original amount of target nucleic acid in the sample by correction of the original amount derived from step (iii) with the aid of the determined amplification efficiency. The efficiency correction of PCR reactions according to the invention for the quantification of nucleic acids can be used for absolute quantification with the aid of an external or internal standard as well as for relative quantification compared to the expression of housekeeping genes.

3 Claims, No Drawings

METHOD FOR REAL-TIME QUANTIFICATION OF NUCLEIC ACIDS

CROSS-REFERENCES TO RELATED APPLICATIONS

This application is a continuation of U.S. patent application Ser. No. 12/549,150, filed Aug. 27, 2009, which is a continuation of U.S. patent application Ser. No. 10/746,993, filed Dec. 24, 2003, which is a continuation of U.S. patent application Ser. No. 09/823,711, filed Mar. 30, 2001, now U.S. Pat. No. 6,691,041, which claims benefit of priority from European Application No. 00107036.6, filed Mar. 31, 2000 and from German Application No. 10034209.4, filed Jul. 13, 2000; the disclosures of each are herein incorporated by reference in their entirety for all purposes.

FIELD OF THE INVENTION

The present invention relates to the field of nucleic acid quantification with the aid of quantitative real-time PCR.

BACKGROUND OF THE INVENTION

Methods for the quantification of nucleic acids are important in many areas of molecular biology and in particular for molecular diagnostics. At the DNA level such methods are used for example to determine the copy numbers of gene sequences amplified in the genome. However, methods for the quantification of nucleic acids are used especially in connection with the determination of mRNA quantities since this is usually a measure for the expression of the respective coding gene.

If a sufficient amount of sample material is available, special mRNAs can be quantified by conventional methods such as Northern Blot analysis or RNAse protection assay methods. However, these methods are not sensitive enough for sample material that is only available in small amounts or for genes that are expressed very weakly.

The so-called RT-PCR is a much more sensitive method. In this method a single-stranded cDNA is firstly produced from the mRNA to be analysed using a reverse transcriptase. Subsequently a double-stranded DNA amplification product is generated with the aid of PCR.

A distinction is made between two different variants of this method:

In the so-called relative quantification the ratio of the expression of a certain target RNA is determined relative to the amount of RNA of a so-called housekeeping gene which is assumed to be constitutively expressed in all cells independent of the respective physiological status. Hence the mRNA is present in approximately the same amount in all cells.

The advantage of this is that different initial qualities of the various sample materials and the process of RNA preparation has no influence on the particular result. However, an absolute quantification is not possible with this method.

Alternatively the absolute amount of RNA used can be determined with the aid of standard nucleic acids of a known copy number and amplification of a corresponding dilution series of this standard nucleic acid. There are two alternatives:

When using external standards the standard and target nucleic acid are amplified in separate reaction vessels. In this case a standard can be used with an identical sequence to the target nucleic acid. However, systematic errors can occur in this type of quantification if the RNA preparation to be analysed contains inhibitory components which impair the efficiency of the subsequent PCR reaction. Such errors can be excluded by using internal standards i.e. by amplifying the standard and target nucleic acid in one reaction vessel. However, a disadvantage of this method is that standards have to be used that have different sequences compared to the target nucleic acid to be analysed in order to be able to distinguish between the amplification of the standard and target nucleic acid. This can in turn lead to a systematic error in the quantification since different efficiencies of the PCR amplification cannot be excluded when the sequences are different.

PCR products can be quantified in two fundamentally different ways:

a) End Point Determination of the Amount of PCR Product Formed in the Plateau Phase of the Amplification Reaction In this case the amount of PCR product formed does not correlate with the amount of the initial copy number since the amplification of nucleic acids at the end of the reaction is no longer exponential and instead a saturation is reached. Consequently different initial copy numbers exhibit identical amounts of PCR product formed. Therefore the competitive PCR or competitive RT-PCR method is usually used in this procedure. In these methods the specific target sequence is coamplified together with a dilution series of an internal standard of a known copy number. The initial copy number of the target sequence is extrapolated from the mixture containing an identical PCR product quantity of standard and target sequence (Zimmermann and Mannhalter, Bio-Techniques 21:280-279, 1996). A disadvantage of this method is also that measurement occurs in the saturation region of the amplification reaction.

b) Kinetic Real-Time Quantification in the Exponential Phase of PCR.

In this case the formation of PCR products is monitored in each cycle of the PCR. The amplification is usually measured in thermocyclers which have additional devices for measuring fluorescence signals during the amplification reaction. A typical example of this is the Roche Diagnostics LightCycler (Cat. No. 2 0110468). The amplification products are for example detected by means of fluorescent labelled hybridization probes which only emit fluorescence signals when they are bound to the target nucleic acid or in certain cases also by means of fluorescent dyes that bind to double-stranded DNA. A defined signal threshold is determined for all reactions to be analysed and the number of cycles Cp required to reach this threshold value is determined for the target nucleic acid as well as for the reference nucleic acids such as the standard or housekeeping gene. The absolute or relative copy numbers of the target molecule can be determined on the basis of the Cp values obtained for the target nucleic acid and the reference nucleic acid (Gibson et al., Genome Research 6:995-1001; Bieche et al., Cancer Research 59:2759-2765, 1999; WO 97/46707; WO 97/46712; WO 97/46714).

In summary in all the described methods for the quantification of a nucleic acid by PCR the copy number formed during the amplification reaction is always related to the copy number formed of a reference nucleic acid which is either a standard or an RNA of a housekeeping gene. In this connection it is assumed that the PCR efficiency of the target and reference nucleic acid are not different.

Usually a PCR efficiency of 2.00 is assumed which corresponds to a doubling of the copy number per PCR cycle (User Bulletin No. 2 ABI Prism 7700, PE Applied Biosystems, 1997).

However, it has turned out that the real PCR efficiency can be different from 2.00 since it is influenced by various factors such as the binding of primers, length of the PCR product, G/C content and secondary structures of the nucleic acid to be amplified and inhibitors that may be present in the reaction mixture as a result of the sample preparation. This is particularly relevant when using heterologous reference nucleic acids e.g. in the relative quantification compared to the expression of housekeeping genes.

SUMMARY OF THE INVENTION

The object of the present invention was therefore to provide methods for the quantification of nucleic acids which overcome the disadvantages of the prior art as described above. The object of the present invention was in particular to provide methods for the quantification of nucleic acids in which a target nucleic acid is quantified independent of the amplification efficiencies of target nucleic acid and reference nucleic acid.

This object is achieved according to the invention by a method for the quantification of a target nucleic acid in a sample comprising the following steps:
a) Determining the amplification efficiency of the target nucleic acid under defined conditions.
b) Amplifying the target nucleic acid contained in the sample under the same reaction conditions.
c) Measuring the amplification in real-time.
d) Quantifying the original amount of target nucleic acid in the sample by correction of the original amount derived from step c) with the aid of the determined amplification efficiency.

According to the invention this method can be used for relative quantification compared to the expression of housekeeping genes as well as for absolute quantification.

A first aspect of the invention therefore concerns a method for quantifying a target nucleic acid in a sample compared to a reference nucleic acid comprising the following steps:
a) Determining the amplification efficiencies of the target nucleic acid and reference nucleic acid under defined amplification conditions
b) Amplifying the target nucleic acid contained in the sample as well as the reference nucleic acid contained in the sample under the same defined amplification conditions.
c) Measuring the amplification of the target nucleic acid and reference nucleic acid in real-time
d) Calculating the original ratio of target nucleic acid and reference nucleic acid in the sample by correcting the ratio derived from step c) with the aid of the amplification efficiencies determined in step a).

A second aspect of the present invention concerns a method for the quantification of a target nucleic acid in a sample comprising the following steps:

a) Determining the amplification efficiencies of the target nucleic acid and of an internal or an external standard under defined amplification conditions
b) Amplifying the target nucleic acid contained in the sample as well as the internal or external standard under the same defined reaction conditions
c) Measuring the amplification of the target nucleic acid and standard in real-time
d) Calculating the original copy number in the sample by correcting the copy number derived from step c) with the aid of the amplification efficiencies determined in step a).

In all methods the amplification efficiencies are preferably determined by
a) preparing a dilution series of the target nucleic acid
b) amplifying the target nucleic acid under defined reaction conditions according to A, the amplification of the nucleic acids being measured in real-time
c) setting a defined signal threshold value
d) determining the cycle number for each dilution at which the signal threshold value is exceeded,
e) calculating the amplification efficiency based on the determined cycle numbers.

DETAILED DESCRIPTION OF THE INVENTION

The object of the invention is achieved by a method for the quantification of a target nucleic acid in a sample comprising the following steps:
a) Determining the amplification efficiency of the target nucleic acid under defined conditions
b) Amplifying the target nucleic acid contained in the sample under the same reaction conditions.
c) Measuring the amplification in real-time
d) Quantifying the original amount of target nucleic acid in the sample by correcting the original amount derived from step c) with the aid of the determined amplification efficiency.

The importance of an efficiency correction will be illustrated by an error calculation. Table 1 shows a theoretical calculation of the average percentage error of the determined copy number in the case of amplification efficiencies that are different from 2.00 as a function of the respective cycle number.

The error is calculated according to the formula $$\text{percentage error} = (2^n/E^n - 1) \times 100$$

in which E is the efficiency of the amplification and n is the respective cycle number at which the percentage error is determined.

TABLE 1

| PCR efficiency (E) | Detection Cycle (n) | | | | | |
| --- | --- | --- | --- | --- | --- | --- |
| | 10 | 15 | 20 | 25 | 30 | 35 |
| 2.00 | — | — | — | — | — | — |
| 1.97 | 16% | 25% | 35% | 46% | 57% | 70% |
| 1.95 | 29% | 46% | 66% | 88% | 113% | 142% |
| 1.90 | 67% | 116% | 179% | 260% | 365% | 500% |
| 1.80 | 187% | 385% | 722% | 1290% | 2260% | 3900% |
| 1.70 | 408% | 1045% | 2480% | 5710% | 13.000% | 29.500% |
| 1.60 | 920% | 2740% | 8570% | 26.400% | 80.700% | 246.400% |

The amplification efficiency can be determined by various methods for example by determining a function with which the measured signal is determined relative to the amplification of the target nucleic acid as a function of the cycle time.

The amplification efficiency is preferably determined by a method in which
a) a dilution series of a target nucleic acid is prepared
b) the target nucleic acid is amplified under defined reaction conditions as claimed in claim 1 and the amplification of the nucleic acid is measured in real-time
c) a defined signal threshold value is set
d) for each dilution the cycle number Cp is determined at which the signal threshold value is exceeded
e) a logarithmic linear function of the copy number of target nucleic acid used for the amplification is determined as a function of the cycle number at which the signal threshold value is exceeded
f) the amplification efficiency E is calculated according to $$E = G^{-a}$$

wherein a is determined as the first derivative of the function determined in step e) and G is the base number of the logarithm.

In a similar manner the amplification efficiency can also be determined by a method in which
a) a dilution series of the target nucleic acid is prepared
b) the target nucleic acid is amplified under defined reaction conditions as claimed in claim 1 and the amplification of the nucleic acid is measured in real-time
c) a defined signal threshold value is set
d) the cycle number Cp at which the signal threshold value is exceeded is determined for each dilution
e) a linear function of the cycle number determined in step d) is determined as a function of a logarithm of the copy number of target nucleic acid used for the amplification and
f) the amplification efficiency E is calculated according to $$E = G^{-1/a}$$

wherein a is determined as the first derivative of the function determined in step e) and G is the base number of the logarithm.

Both preferred procedures have the advantage that a systematic error cannot occur that results from determining the amplification efficiency in a phase of the PCR reaction in which there is no longer an exponential amplification of the target nucleic acid (plateau phase).

However, it unexpectedly turned out that under certain conditions the amplification efficiency can also be dependent on the original amount of target nucleic acid or it can change during the first cycles of an amplification reaction that is still in the exponential phase. A subject matter of the invention is thus also a method for the efficiency-corrected quantification of nucleic acids in which the efficiency of the amplification is determined by
a) preparing a dilution series of the target nucleic acid
b) amplifying the target nucleic acid under defined reaction conditions as claimed in claim 1 and measuring the amplification of the nucleic acid in real-time
c) setting a defined signal threshold value
d) determining the cycle number Cp at which the signal threshold value is exceeded for each dilution
e) determining the amplification efficiency as a function of the amount of target nucleic acid.

This can for example be achieved by derivation of a continuously differentiable function F(Cp) of the Cp values as a function of the original copy number or vice versa.

The function F(Cp)=log (concentration of the original copy number) can for example be standardized by mathematical algorithms such as a polynomial fit of a higher degree. The amplification efficiency E can then be determined by the equation $$E = G^{-dF(Cp)/dCp}$$

in which dF/(Cp) is the derivative of the continuous function and G is the base number of the logarithm. A polynomial fit of the 4$^{th}$ degree has proven to be particularly suitable within the sense of the invention.

The efficiency-corrected quantification of nucleic acids according to the invention can in principle be used for methods for absolute quantification as well as for methods for relative quantification.

Hence a subject matter of the present invention in relation to relative quantification is also a method for the quantification of a target nucleic acid in a sample relative to a reference nucleic acid comprising the following steps:
  a) Determination of the amplification efficiencies of the target nucleic acid and of the reference nucleic acid under defined amplification conditions.
  b) Amplification of the target nucleic acid contained in the sample as well as of the reference nucleic acid contained in the sample under the same defined amplification conditions.
  c) Measurement of the amplification of the target nucleic acid and of the reference nucleic acid in real-time.
  d) Calculation of the original ratio of target nucleic acid and reference nucleic acid in the sample by correcting the ratio derived from step c) with the aid of the amplification efficiencies determined in step a).

Such a method according to the invention eliminates on the one hand the influence of inhibitors that may be present in the examined sample and, on the other hand, corrects errors which may occur as a result of different amplification efficiencies of the target nucleic acid and reference nucleic acid.

Steps b) to d) are advantageously carried out in a parallel mixture containing a so-called calibrator sample. The calibrator sample is a sample which contains the target nucleic acid and reference nucleic acid in a defined ratio that is constant for each measurement. Subsequently the ratio of the quotients determined for the sample and for the calibrator sample is determined as a measure for the original amount of target nucleic acid in the sample. This has the advantage that in addition other systematic errors are eliminated that are due to differences in the detection sensitivity of the target nucleic acid and reference nucleic acid. Such systematic errors can for example occur as a result of different hybridization properties of the hybridization probes or, in the case of fluorescent-labelled probes, different excitation efficiencies, quantum yields or coupling efficiencies of the dye to the probe. Therefore the sample to be tested and the calibrator sample must be analysed in each experiment with the same detection agents i.e. with the same batch of fluorescent-labelled hybridization probes.

A special embodiment of relative quantification according to the invention is a method for the quantification of a target nucleic acid in a sample relative to a reference nucleic acid comprising the following steps:
  a) Determination of the amplification efficiencies of the target nucleic acid and of the reference nucleic acid under defined amplification conditions
  b) Amplification of the target nucleic acid contained in the sample and of the reference nucleic acid contained in the sample under the same defined amplification conditions.
  c) Measurement of the amplification of the target nucleic acid and of the reference nucleic acid in real time.
  d) Determination of a defined signal threshold value.
  e) Determination of the cycle numbers at which the signal threshold value is in each case exceeded during the amplification of the target nucleic acid and the reference nucleic acid.

f) Calculation of the original ratio of target nucleic acid and reference nucleic acid in the sample according to the formula $$N(T)_0/N(R)_0 = E(R)^{n(R)}/E(T)^{n(T)}, \text{ wherein}$$

$N(T)_0$=the original amount of target DNA present in the sample
$N(R)_0$=the original amount of reference DNA present in the sample
$E(R)$=the amplification efficiency of the reference nucleic acid
$n(R)$=the cycle number of the reference nucleic acid measured in step e)
$E(T)$=the amplification efficiency of the target nucleic acid
$n(T)$=the cycle number of the target nucleic acid measured in step e)

In this embodiment it is advantageous to carry out steps b), c), e) and f) with a calibrator sample in order to eliminate systematic errors due to the detection of amplification products and subsequently the ratio of the quotients measured for the sample and for the calibrator sample are determined as a measure for the original amount of target nucleic acid in the sample.

The ratio obtained in step f) is calculated according to the invention as follows:

$$N(T)_n = N(T)_0 \times E(T)^{n(T)} \quad (1)$$

$$N(R)_n = N(R)_0 \times E(R)^{n(R)} \quad (2)$$

in which $N(T)_n$=the amount of target DNA at the signal threshold value
and $N(R)_n$=the amount of reference DNA at the signal threshold value From (1) and (2) it follows that:

$$\frac{N(T)_n}{N(R)_n} = \frac{N(T)_0 \times E(T)^{n(T)}}{N(R)_0 \times E(R)^{n(R)}} \quad (3)$$

From this it follows that:

$$\frac{N(T)_0}{N(R)_0} = \frac{N(T)_n \times E(R)^{n(R)}}{N(R)_0 \times E(T)^{n(T)}} \quad (4)$$

Due to the fact that an identical signal threshold value has been set for the target and reference nucleic acid this may be approximated to:

$$N(T)_n = N(R)_n.$$

Under this condition and starting from equation (4) for the original ratio of target nucleic acid and reference nucleic acid, this results in the equation $$N(T)_0/N(R)_0 = E(R)^{n(R)}/E(T)^{n(T)} \quad (5)$$

However, this assumed approximation does not apply when target nucleic acid and reference nucleic acid are detected with different sensitivities. According to the invention it is therefore particularly advantageous to measure a calibrator sample in a parallel reaction and to determine the ratio of the quotients $N(T)_0/N(R)_0$ measured for the sample and for the calibrator sample as a measure for the original amount of target nucleic acid in the sample.

This results in the following from equation (4) using the indices $_A$ for the sample to be analysed and $_K$ for the calibrator sample $$\frac{N(T)_{0A}}{N(R)_{0A}} \bigg/ \frac{N(T)_{0K}}{N(R)_{0K}} = \frac{\frac{N(T)_{nA} \times E(R)^{nA(R)}}{N(R)_{nA} \times E(T)^{nA(T)}}}{\frac{N(T)_{nK} \times E(R)^{nK(R)}}{N(R)_{nK} \times E(T)^{nK(T)}}} \quad (6)$$

Due to the fact that an identical signal threshold value has been set for the sample to be analysed and for the calibrator sample and that identical agents are used to detect target and reference amplicons in the sample and in the calibrator sample, the ratio of the quotient determined for the sample and for the calibrator sample is as follows:

$$\frac{N(T)_{nA}}{N(R)_{nA}} \bigg/ \frac{N(T)_{nK}}{N(R)_{nK}} = 1$$

Hence the ratio of the quotients of the sample to be analysed and the calibrator sample is:

$$\frac{N(T)_{0A}}{N(R)_{0A}} \bigg/ \frac{N(T)_{0K}}{N(R)_{0K}} = E(R)^{nA(R)-nK(R)} * E(T)^{nk(T)-nA(T)} \quad (7)$$

Consequently a relative value can be obtained in this manner for the original copy number of target nucleic acid in the sample in which systematic errors due to different amplification efficiencies as well as due to different detection sensitivities have been eliminated. The only requirement for the accuracy of the determined value is the justified assumption that under absolutely identical buffer conditions the amplification and detection efficiencies are also identical in the various reaction vessels.

Requirement for all methods according to the invention for relative quantification is that the amplification efficiency of the target nucleic acid as well as the amplification efficiency of the reference nucleic acid are determined. Both of these determinations are preferably carried out by the methods described above by determining the cycle number at which a certain signal threshold value is exceeded.

In a preferred embodiment of relative quantification the sample is divided into two aliquots and the real-time measurement of the amplification of the target nucleic acid and reference nucleic acid is carried out in separate reaction vessels. This prevents interference between the amplification reactions of the target nucleic acid and the reference nucleic acid with regard to their efficiency for example by competition for deoxynucleotides or Taq polymerase. Furthermore the target nucleic acid and reference nucleic acid can be detected with the same detection systems, for example with the same DNA binding dye.

Alternatively the real-time measurement of the amplification of target nucleic acid and reference nucleic acid can be carried out in one sample in the same reaction vessel using differently labelled hybridization probes. This is particularly advantageous when only small amounts of sample material are available because the number of PCR reactions required is halved in this manner.

If it is intended to determine the absolute amount of target nucleic acid to be detected in a sample, then the method for the quantification of a target nucleic acid in a sample comprises the steps of:

a) Determination of the amplification efficiencies of the target nucleic acid and of an internal or external standard under defined amplification conditions;
b) Amplification of the target nucleic acid contained in the sample as well as of the internal or external standard under the same defined reaction conditions;
c) Measurement of the amplification of the target nucleic acid and standard in real time; and
d) Calculation of the original copy number in the sample by correcting the copy number derived from step c) with the aid of the amplification efficiencies determined in step a).

The sequences of the target nucleic acid and standard nucleic acid are advantageously substantially identical. However, when selecting the sequence for an internal standard it must be taken into account that the available detection system should be able to distinguish between the standard and target nucleic acid. This can for example be achieved by using hybridization probes with different labels for the detection of the target nucleic acid and internal standard. Ideally oligonucleotides are used for this as detection probes which can be used to distinguish between minimal sequence differences such as point mutations.

An advantage of using an internal standard is that the inhibitors present in the sample also influence the amplification of the standard. Hence differences in the amplification efficiencies can be minimized.

In contrast the use of an external standard has the advantage that the amplification reactions of the target nucleic acid and standard cannot competitively interfere with one another with regard to their efficiency. Moreover the amplification products of the standard and target nucleic acid can be detected in parallel reactions with the aid of the same detection system for example with the same hybridization probe. A disadvantage is possible differences in the PCR efficiencies due to inhibitors in the sample. However, errors in the quantification caused by this can be eliminated by the method described in the following:

In a preferred embodiment for the absolute quantification of a target nucleic acid in a sample the method according to the invention comprises the following steps:
a) Determination of the amplification efficiencies of the target nucleic acid as well as of an internal or external standard under defined amplification conditions
b) Amplification of the target nucleic acid contained in the sample as well as of the internal or external standard under the same defined reaction conditions
c) Measurement of the amplification of target nucleic acid and standard in real-time
d) Setting a defined signal threshold value
e) Determination of the cycle number during the amplification of target nucleic acid and standard at which the signal threshold value is exceeded
f) Determination of the original copy number $N(T)_0$ of the target nucleic acid in the sample according to the formula $$N(T)_0 = N(S)_0 * E(S)^{n(S)} / E(T)^{n(T)} \quad (8)$$ in which $N(S)_0$ = the original amount of standard used
$E(S)$ = the amplification efficiency of the standard
$n(S)$ = the cycle number of the standard measured in step e)
$E(T)$ = the amplification efficiency of the standard
$n(T)$ = the cycle number of the target nucleic acid measured in step e).

In this case like the relative quantification, the amplification efficiencies of the target nucleic acid and the internal standard are preferably determined as described by determining the cycle number at which a certain signal threshold value is exceeded.

According to the invention $N(T)_0$ is calculated as follows:

$$N(T)_n = N(T)_0 * E(T)^{n(T)}$$

and $$N(S)_n = N(S)_0 * E(S)^{n(S)}$$

Since an identical signal threshold value has been set for the target and standard nucleic acid this approximates to:

$$N(T)n = N(S)n$$

Hence the original copy number of target nucleic acid present in the sample is calculated according to the equation $$N(T)_0 = N(S)_0 * E(S)^{n(S)} / E(T)^{n(T)} \quad (8)$$

The invention in particular also concerns those embodiments of the described methods for the efficiency-corrected quantification of nucleic acids in which the amplification products are detected by hybridization probes which can be labelled with a detectable component in many different ways.

A prerequisite for the efficiency-corrected determination of the original amount of a target nucleic acid and for the determination of the amplification efficiencies per se is to define signal threshold values and subsequently determine the cycle number for the respective amplification reaction at which a certain signal threshold value is reached. The signal threshold value can be determined according to the prior art in various ways:

According to the prior art the signal threshold value can for example be a signal which corresponds to a certain multiple of the statistical variance of the background signal (ABI Prism 7700 Application Manual, Perkin Elmer).

Alternatively the cycle number at which the signal threshold value is exceeded can be determined according to the so-called "fit point above threshold" method (LightCycler Operator's Manual, B59-B68, Roche Molecular Biochemicals, 1999).

In a further embodiment the threshold value can be determined as a relative value instead of an absolute value when, independently of the absolute value of the signal, the course of the amplification reaction is determined as a function of the cycle number and subsequently the $n^{th}$ derivative is calculated. In this case exceeding certain extremes can be defined as exceeding a certain signal threshold value (EP Application No. 0016523.4). Hence this method of determining the threshold value is independent of the absolute signal strength of for example a fluorescence signal. Thus it is particularly suitable for those embodiments in which the target nucleic acid and reference nucleic acid are amplified in the same reaction vessel and are detected with the aid of different fluorescent labels. Methods have proven to be particularly suitable for the efficiency-corrected quantification of PCR products in which the maximum of the second derivative is determined as a measure for the signal threshold value.

The hybridization probes used for the methods according to the invention are usually single-stranded nucleic acids such as single-stranded DNA or RNA or derivatives thereof or alternatively PNAs which hybridize at the annealing temperature of the amplification reaction to the target nucleic acid. These oligonucleotides usually have a length of 20 to 100 nucleotides.

Depending on the detection format the label can be introduced on any ribose or phosphate group of the oligonucleotide. Labels at the 3' and 5' end of the nucleic acid molecule are preferred.

The type of label must be detectable in the real-time mode of the amplification reaction. This is for example in principle also (but not only) possible with the aid of labels that can be detected by NMR.

Methods are particularly preferred in which the amplified nucleic acids are detected with the aid of at least one fluorescent-labelled hybridization probe.

Many test procedures are possible for this. The following three detection formats have proven to be particularly suitable in connection with the present invention:

a) FRET Hybridization Probes

For this test format 2 single-stranded hybridization probes are used simultaneously which are complementary to adjacent sites of the same strand of the amplified target nucleic acid. Both probes are labelled with different fluorescent components. When excited with light of a suitable wavelength, a first component transfers the absorbed energy to the second component according to the principle of fluorescence resonance energy transfer such that a fluorescence emission of the second component can be measured when both hybridization probes bind to adjacent positions of the target molecule to be detected.

Alternatively it is possible to use a fluorescent-labelled primer and only one labelled oligonucleotide probe (Bernard et al., Analytical Biochemistry 235, p. 1001-107 (1998)).

b) TaqMan Hybridization Probes

A single-stranded hybridization probe is labelled with two components. When the first component is excited with light of a suitable wavelength, the absorbed energy is transferred to the second component, the so-called quencher, according to the principle of fluorescence resonance energy transfer. During the annealing step of the PCR reaction, the hybridization probe binds to the target DNA and is degraded by the 5'-3' exonuclease activity of the Taq polymerase during the subsequent elongation phase. As a result the excited fluorescent component and the quencher are spatially separated from one another and thus a fluorescence emission of the first component can be measured.

c) Molecular Beacons

These hybridization probes are also labelled with a first component and with a quencher, the labels preferably being located at both ends of the probe. As a result of the secondary structure of the probe, both components are in spatial proximity in solution. After hybridization to the target nucleic acid both components are separated from one another such that after excitation with light of a suitable wavelength the fluorescence emission of the first component can be measured (Lizardi et al., U.S. Pat. No. 5,118,801).

In the described embodiments in which only the target nucleic acid or only the reference nucleic acid or an external standard is amplified in one reaction vessel in each case, the respective amplification product can also be detected according to the invention by a DNA binding dye which emits a corresponding fluorescence signal upon interaction with the double-stranded nucleic acid after excitation with light of a suitable wavelength. The dyes SybrGreen and SybrGold (Molecular Probes) have proven to be particularly suitable for this application. Intercalating dyes can alternatively be used.

A subject matter of the invention are also kits that contain appropriate agents to carry out the method according to the invention. According to the invention these agents are present in the kit in various compositions. A kit preferably contains reagents such as for example a reverse transcriptase for preparing a cDNA, DNA polymerase for the amplification reaction, specific primers for the amplification reaction and optionally also specific hybridization probes to detect the amplification product. As an alternative polymerases for a single-step RT-PCR reaction can be present in the kit. It is also possible that a kit according to the invention contains package inserts or disks containing files with previously determined amplification efficiencies for defined amplification conditions. Finally the invention also concerns a kit which additionally contains further reagents for the synthesis and labelling of oligonucleotides such as fluorescent NHS-esters or fluorescent-labelled CPGs. Moreover a kit according to the invention can optionally also contain a DNA which can be used as an internal or external standard.

EXAMPLES

The invention is further elucidated by the following examples:

Example 1

Amplification of Cytokeratin 20 (CK20) and Porphobilinogen (PBGD) cDNAs

RNA was isolated from the cell line HT-29 (ATCC) using a HighPure-RNA Restriction Kit (Roche Diagnostics GmbH). After semi-quantitative spectrophotometric determination, the RNA concentration was adjusted to 100 ng/µl in RNA-free water. Three serial single dilutions were prepared from this with RNA concentrations of 10 ng, 1 ng and 100 pg/µl.

Total cDNA was prepared from these dilutions by reverse transcription under the following conditions:

| | |
|---|---|
| 1x | AMV reverse transcription buffer |
| 1 mM | of each deoxynucleoside triphosphate |
| 0.0625 mM | randomized hexamers |
| 10 u | AMV reverse transcriptase |
| 10 µl | RNA |
| Ad. 20 µl | water |

All mixtures were incubated for 10 minutes at 25° C., 30 minutes at 42° C. and 5 minutes at 95° C. for the cDNA synthesis. Subsequently they were cooled to 4° C. A sample containing 10 ng/µl HT29 RNA was used as a calibrator.

Afterwards the amplification reaction was carried out which was measured in real-time in the FRET HybProbe format on a LightCycler instrument (Roche Diagnostics GmbH). Each reaction mixture was amplified under the following conditions:

| | |
|---|---|
| 1x | fast start DNA hybridization probes buffer |
| 1x | detection mix |
| 2 µl | cDNA |
| Ad. 20 µl | water |

The 1× detection mix was composed of 0.5 µM forward and 0.5 µM reverse primers, each, 0.2 µM fluorescein and LC-Red 640 labelled hybridization probes, 4 mM magnesium chloride and 0.005% Brij-35.

Primers having SEQ ID NO:1 and SEQ ID NO:2 were used to amplify a CK20 sequence. The CK20 product was detected using a fluorescein probe having SEQ ID NO:3 and a LC-Red 640 hybridization probe having SEQ ID NO:4. Primers having SEQ ID NO:5 and 6 were used to detect the PBGD sequence. PBGD was detected using a fluorescein-labelled hybridization probe having SEQ ID NO:7 and an LC-Red 640-labelled hybridization probe having SEQ ID NO:8.

The reaction mixtures were firstly incubated for 10 minutes at 95° C. in the presence of 5 mM magnesium chloride for the amplification. The actual amplification reaction was carried out for 50 cycles according to the following scheme:
10 sec. 95° C.
10 sec. 60° C.
5 sec. 72° C.

After each incubation at 60° C. a fluorescence measurement was carried out according to the manufacturer's instructions. The Cp value was determined as the maximum of the $2^{nd}$ derivative of the amplification reaction as a function of the cycle number.

Example 2

Determination of the Efficiency of the Amplification of CK20 and PBGD

A function was established to determine the efficiency in which the cycle number Cp determined for the respective concentration was determined as a function of the decadic logarithm of the RNA concentration used.

A linear function was calculated from this function by regression analysis with the aid of the LightCycler software. Starting from this function the efficiency was determined according to the equation $$\text{efficiency} = 10^{-1/a}$$

wherein $a$ is the gradient ($1^{st}$ derivative) of the determined regression line.

TABLE 2

| Conc (ng) | Log (ng) | Cp-CK20 | Cp-PBGD |
|---|---|---|---|
| 0.1 | −1.0 | 35.73 | 38.73 |
| 1 | 0.0 | 30.13 | 33.59 |
| 10 | 1.0 | 24.20 | 28.63 |
| Efficiency: | | 1.491 | 1.578 |

Cp: measured cycle number

The results obtained for CK20 and PBGD are shown in Table 2. The result shows that on the one hand the efficiencies are considerably different from 2.00 i.e. a doubling of the target nucleic acid does not take place with each PCR cycle. On the other hand, the result shows that the efficiencies of the amplification of CK20 and PBGD differ significantly from one another under otherwise identical conditions.

Example 3

Determination of the Original Ratio of Target Nucleic Acid and Reference Nucleic Acid with and without Correction of the Amplification Efficiency Under the conditions described in Example 1 the ratio determined of the original amount of CK20 and PBGD should be independent of the respective amplified concentration of the sample material used. Hence the determination of the ratio for various amounts of sample RNA was used to check the effect of an efficiency correction on the basis of the measured values that were obtained. In this case the ratio of CK20 to PBGD was determined according to the invention according to equation (5). On the one hand, the ratio was determined using the efficiencies obtained from example 2 and on the other hand with an assumed amplification efficiency of 2.00 for CK20 and for PGD. The results are shown in Table 3:

TABLE 3

| HT29 (ng) | CP CK20 | Cp PBGD | $N(T)_0/N(R)_0$ Efficiency = 2 | $N(T)_0/N(R)_0$ Efficiency corrected |
|---|---|---|---|---|
| 0.1 ng | 35.73 | 38.73 | 8.00 | 29.68 |
| 1 ng | 30.13 | 33.59 | 11.00 | 26.66 |
| 10 ng | 24.20 | 28.63 | 21.56 | 29.66 |
| | | M: | 13.52 | 28.66 |
| | | SD: | 7.12 | 1.74 |
| | | % CV: | 52.7% | 6.1% |

Cp = measured cycle number
M = mean
SD = standard deviation
% CV = coefficient of variation As can be seen from the table, the efficiency-corrected values calculated for the ratio of $N(T)_0/N(R)_0$ have a significantly lower standard deviation for the various amounts of sample RNA than the uncorrected values and a coefficient of variation of 6.1% compared to 52.7%.

Example 4

Efficiency-Correction when Using a Calibrator

Analogously to Examples 1 and 2 amplification reactions were carried out in the presence of 10 mM magnesium chloride. In this case an efficiency of 1.491 was determined for CK20 and an efficiency of 1.578 was determined for PBGD. In addition the Cp values of a calibrator sample containing an unknown amount of HT-29 RNA was determined at 5 mM and 10 mM magnesium chloride. The measured data were used to determine the quotients of the ratios of CK20 to PBGD between the samples analysed in each case and the appropriate calibrator according to equation (7). This determination was carried out on the one hand with an assumed efficiency of 2 for the amplification of CK20 and PBGD as well as, on the other hand, with the aid of experimentally determined amplification efficiencies. The result is shown in Table 4.

TABLE 4

| $MgCl_2$ | HT29 (ng) | Cp CK20 | Cp PBGD | T:R/C Efficiency | T:R/C Efficiency corrected |
|---|---|---|---|---|---|
| 5 mM | 0.1 ng | 36.59 | 39.09 | 0.76 | 0.92 |
| 5 mM | 1 ng | 30.60 | 32.60 | 0.54 | 0.72 |
| 5 mM | 10 ng | 25.19 | 27.95 | 0.91 | 0.95 |
| calibrator | Cal. | 24.78 | 27.67 | 1.00 | 1.00 |
| 10 mM | 0.1 ng | 35.73 | 38.73 | 0.39 | 1.04 |
| 10 mM | 1 ng | 30.13 | 33.59 | 0.53 | 0.93 |
| 10 mM | 10 ng | 24.20 | 28.63 | 1.04 | 1.04 |
| calibrator | Cal. | 24.01 | 28.38 | 1.00 | 1.00 |
| | | | M: | 0.70 | 0.93 |
| | | | SD: | 0.26 | 0.10 |
| | | | % CV: | 36.7% | 11.1% |

$$T:R/C = \frac{\frac{N(T)_{0A}}{N(R)_{0A}}}{\frac{N(T)_{0K}}{N(R)_{0K}}}$$

Cp = measured cycle number
M = mean
SD = standard deviation
% CV = coefficient of variation As can be seen in Table 4, the efficiency-corrected values have a lower standard deviation (0.10) as well as a three-fold lower coefficient of variation than the T:R/C values with an assumed PCR efficiency of 2.00. This result shows that an efficiency correction according to the invention is also advantageous in quantifications in which a standardization with the aid of calibrators has already been carried out.

Example 5

Absolute Quantification of Plasmid DNA

A decadic dilution series of a plasmid containing the PSA gene of $10^9$ to $10^2$ copies was prepared for this purpose. At the same time a second decadic dilution series with a plasmid containing the gene for TNF (tumour necrosis factor) with an unknown copy number of plasmid DNA was prepared. Afterwards the PSA reaction mixtures were amplified on a Light-Cycler (Roche Diagnostics) under standard conditions using the primers having SEQ ID NO:9 and 10 and the TNF reaction mixtures were amplified using the primers having SEQ ID NO:11 and 12 (Roche Diagnostics LightCycler SybrGreen Mastermix, 5 mM final concentration $MgCl_2$, 0.5 µM final concentration of each primer). The amplification was measured in real-time using the DNA binding agent SybrGreenI (Molecular Probes) under standard conditions in which the evaluation was carried out according to the manufacturer's instructions in the second derivative mode.

The original copy number of the TNF plasmid was determined in two different ways on the basis of the obtained data.

On the one hand a calibration line based on the PSA amplification was generated assuming the same amplification efficiency for PSA and TNF.

On the other hand the original copy number was determined according to formula (8). Analogously to example 2 the amplification efficiency for PSA and TNF was determined by calculating a regression line according to the formula $$E = 10^{-1/a}$$

wherein a denotes the increase ($1^{st}$ derivative) of the calculated regression line. In this case an amplification efficiency of 2.03 was determined for PSA and an amplification efficiency of 2.13 was determined for TNF.

The results of the two different quantification procedures are shown in Table 5. A so-called dilution check was carried out as a measure for the accuracy of the determination. The values denoted dilution check are calculated from the quotients of the copy numbers measured for the respective dilution of two dilution mixtures that differ from one another by a factor of 10. Thus a value of 10.00 would be expected as the ideal value.

TABLE 5

| Dilution | Not efficiency corrected | | Efficiency corrected | |
|---|---|---|---|---|
| | Determined copy number per dilution | Dilution check | Determined copy number per dilution | Dilution check |
| 1 | 30826128 | 10.10 | 27728632 | 12.12 |
| $10^{-1}$ | 3053000 | 13.82 | 2287050 | 14.98 |
| $10^{-2}$ | 220900 | 7.19 | 152643 | 7.94 |
| $10^{-3}$ | 30710 | 11.61 | 19227 | 13.89 |
| $10^{-4}$ | 2646 | 8.55 | 1384 | 9.52 |
| $10^{-5}$ | 309.5 | 7.61 | 145.4 | 8.76 |
| $10^{-6}$ | 40.66 | 3.86 | 16.6 | 3.84 |
| $10^{-7}$ | 10.54 | | 4.3 | |
| Mean: | | 8.96 | | 10.16 |

As the result of the dilution check from Table 5 shows, the mean of the efficiency-corrected data results in a value of 10.16, whereas the mean of non-efficiency-corrected data results in a value of 8.96 which is considerably further away from the ideal value of 10.00. From this it follows that an efficiency correction is also advantageous for embodiments in which an absolute quantification of nucleic acids with the aid of PCR is carried out.

The present invention is not to be limited in scope by the exemplified embodiments which are intended as illustrations of single aspects of the invention. Various modifications of the invention in addition to those described herein will become apparent to those skilled in the art from the foregoing description and accompanying drawings. Such modifications are intended to fall within the scope of the appended claims. All publications cited herein are incorporated by reference in their entirety.

What is claimed is:

1. A method for the quantification of a target nucleic acid in a test sample relative to a reference nucleic acid comprising:
   a) determining amplification efficiencies of the target nucleic acid and of the reference nucleic acid under defined amplification conditions,
   b) amplifying the target nucleic acid contained in the test sample and the reference nucleic acid contained in the test sample under the same defined reaction conditions,
   c) measuring the amplification of the target nucleic acid and of the reference nucleic acid in real time to determine amplified amounts of target nucleic acid and reference nucleic acid and calculating the ratio of the target nucleic acid and the reference nucleic acid in the test sample as a function of the amplification efficiencies determined in step a) and cycle number,
   d) amplifying the target nucleic acid contained in a calibrator sample and the reference nucleic acid contained in the calibrator sample under the same defined reaction conditions,
   e) measuring the amplification of the target nucleic acid from the calibrator sample and of the reference nucleic acid from the calibrator sample in real time to determine amplified amounts of the target nucleic acid and the reference nucleic acid from the calibrator sample and calculating the ratio of the target nucleic acid and the reference nucleic acid in the calibrator sample as a function of the amplification efficiencies determined in step a) and cycle number, and
   f) quantifying the target nucleic acid in the test sample relative to the reference nucleic acid as a function of a quotient of (i) said ratio of the target nucleic acid and the reference nucleic acid in the test sample and (ii) said ratio of the target nucleic acid and the reference nucleic acid in the calibrator sample.

2. The method of claim 1, wherein the efficiency of the amplification is determined by
   a) preparing a dilution series of the target nucleic acid and the reference nucleic acid,
   b) amplifying the target nucleic acid and the reference nucleic acid under defined reaction conditions as claimed in claim 1, the amplification of the nucleic acid being measured in real time,
   c) determining a defined threshold value,
   d) determining the cycle number at which the signal threshold value is exceeded for each dilution,
   e) determining a logarithmic linear function of the copy number of target nucleic acid and reference nucleic acid used for the amplification as a function of the cycle number at which the signal threshold value is exceeded and
   f) calculating the amplification efficiency E according to
   $$E = G-a,$$
   wherein $a$ is determined as the first derivative of the function determined in step e) and G is the base number of the logarithm.

3. The method of claim 1, wherein the efficiency of the amplification is determined by
   a) preparing a dilution series of the target nucleic acid and the reference nucleic acid,
   b) amplifying the target nucleic acid and the reference nucleic acid under defined reaction conditions as claimed in claim 1, the amplification of the nucleic acid being measured in real time,
   c) determining a defined signal threshold value,
   d) determining the cycle number at which the signal threshold value is exceeded for each dilution,
   e) determining a linear function of the cycle number determined in step d) as a function of a logarithm of the copy number of target nucleic acid and the reference nucleic acid used for the amplification and
   f) calculating the amplification efficiency E according to
   $$E = G^{-1/a},$$
   wherein $a$ is determined as the first derivative of the function determined in step e) and G is the base number of the logarithm.

* * * * *

SEQUENCE LISTING

<160> NUMBER OF SEQ ID NOS: 12

<210> SEQ ID NO 1
<211> LENGTH: 20
<212> TYPE: DNA
<213> ORGANISM: Homo sapiens

<400> SEQUENCE: 1
atcaagcagt ggtacgaaac                    20

<210> SEQ ID NO 2
<211> LENGTH: 18
<212> TYPE: DNA
<213> ORGANISM: Homo sapiens

<400> SEQUENCE: 2
aggacacacc gagcattt                                                    18

<210> SEQ ID NO 3
<211> LENGTH: 25
<212> TYPE: DNA
<213> ORGANISM: Homo sapiens

<400> SEQUENCE: 3
attacagaca aattgaagag ctgcg                                            25

<210> SEQ ID NO 4
<211> LENGTH: 25
<212> TYPE: DNA
<213> ORGANISM: Homo sapiens

<400> SEQUENCE: 4
agtcagatta aggatgctca actgc                                            25

<210> SEQ ID NO 5
<211> LENGTH: 19
<212> TYPE: DNA
<213> ORGANISM: Homo sapiens

<400> SEQUENCE: 5
gcggagccat gtctggtaa                                                   19

<210> SEQ ID NO 6
<211> LENGTH: 20
<212> TYPE: DNA
<213> ORGANISM: Homo sapiens

<400> SEQUENCE: 6
ccagggtacg aggctttcaa                                                  20

<210> SEQ ID NO 7
<211> LENGTH: 24
<212> TYPE: DNA
<213> ORGANISM: Homo sapiens

<400> SEQUENCE: 7
gagagtgatt cgcgtgggta cccg                                             24

<210> SEQ ID NO 8
<211> LENGTH: 25
<212> TYPE: DNA
<213> ORGANISM: Homo sapiens

<400> SEQUENCE: 8
agagccagct tgctcgcata cagac                                            25

<210> SEQ ID NO 9
<211> LENGTH: 22
<212> TYPE: DNA
<213> ORGANISM: Homo sapiens

<400> SEQUENCE: 9
gaggagttct tgaccccaaa ga                                               22

<210> SEQ ID NO 10
<211> LENGTH: 18
<212> TYPE: DNA
<213> ORGANISM: Homo sapiens

<400> SEQUENCE: 10

-continued

```
tccagcgtcc agcacaca                                              18

<210> SEQ ID NO 11
<211> LENGTH: 20
<212> TYPE: DNA
<213> ORGANISM: Homo sapiens

<400> SEQUENCE: 11
cctgccccaa tccctttatt                                            20

<210> SEQ ID NO 12
<211> LENGTH: 21
<212> TYPE: DNA
<213> ORGANISM: Homo sapiens

<400> SEQUENCE: 12
ggtttcgaag tggtggtctt g                                          21
```